United States Patent [19]

Hempel et al.

[11] Patent Number: 5,383,861
[45] Date of Patent: Jan. 24, 1995

[54] FLEXIBLE CANNULA

[75] Inventors: Sven Hempel, Kaltenkirchen; Thomas Wulf, Hamburg, both of Germany

[73] Assignee: Ethicon Endo-Surgery, Cincinnati, Ohio

[21] Appl. No.: 135,216

[22] Filed: Oct. 12, 1993

[30] Foreign Application Priority Data

Oct. 16, 1992 [DE] Germany .................. 4234990

[51] Int. Cl.6 ................. A61M 39/00; A61M 39/04
[52] U.S. Cl. ..................... 604/167; 604/164; 604/256
[58] Field of Search .......... 604/157, 158, 164, 165, 604/167, 266, 264, 274, 169

[56] References Cited

U.S. PATENT DOCUMENTS

| 4,000,739 | 1/1977 | Stevens | 604/169 |
|---|---|---|---|
| 4,368,730 | 1/1983 | Sharrock | 604/158 |
| 4,424,833 | 1/1984 | Spector et al. | 604/167 |
| 4,535,773 | 8/1985 | Yoon | 604/169 |
| 4,634,432 | 1/1987 | Kocak | 604/167 |
| 4,960,412 | 10/1990 | Fink | 604/167 |
| 5,053,016 | 10/1991 | Lander | 604/169 |
| 5,125,903 | 7/1992 | McLaughlin et al. | 604/167 |
| 5,129,885 | 7/1992 | Green | 604/164 |
| 5,141,498 | 8/1992 | Christian | 604/167 |
| 5,201,714 | 4/1993 | Gentelia et al. | 604/167 |
| 5,209,737 | 5/1993 | Ritchart et al. | 604/256 |
| 5,226,426 | 7/1993 | Yoon | 604/165 |
| 5,226,891 | 7/1993 | Bushatz et al. | 604/165 |
| 5,242,412 | 9/1993 | Blake, III | 604/167 |

FOREIGN PATENT DOCUMENTS

| 7430345 | 12/1974 | Germany | A61B 1/00 |
|---|---|---|---|
| 8914955.6 | 6/1990 | Germany | A61B 17/34 |

Primary Examiner—Paul J. Hirsch
Attorney, Agent, or Firm—Paul A. Coletti

[57] ABSTRACT

A flexible cannula consists of a flexible tube, whose distal zone is introducible into the inside of the body through a trocar puncture point, and a top piece. The top piece is divided into a housing which is flat when seen in the direction of the longitudinal axis of the cannula and which is secured at the proximal end of the tube and contains a closure device and a flexible intermediate tube which, starting from the proximal end wall of the housing, extends along the longitudinal axis of the cannula.

8 Claims, 2 Drawing Sheets

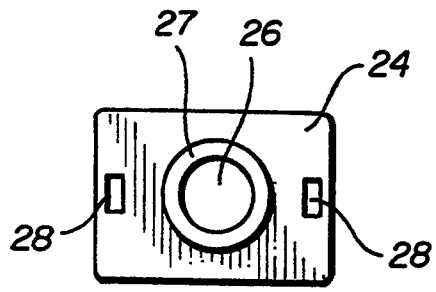
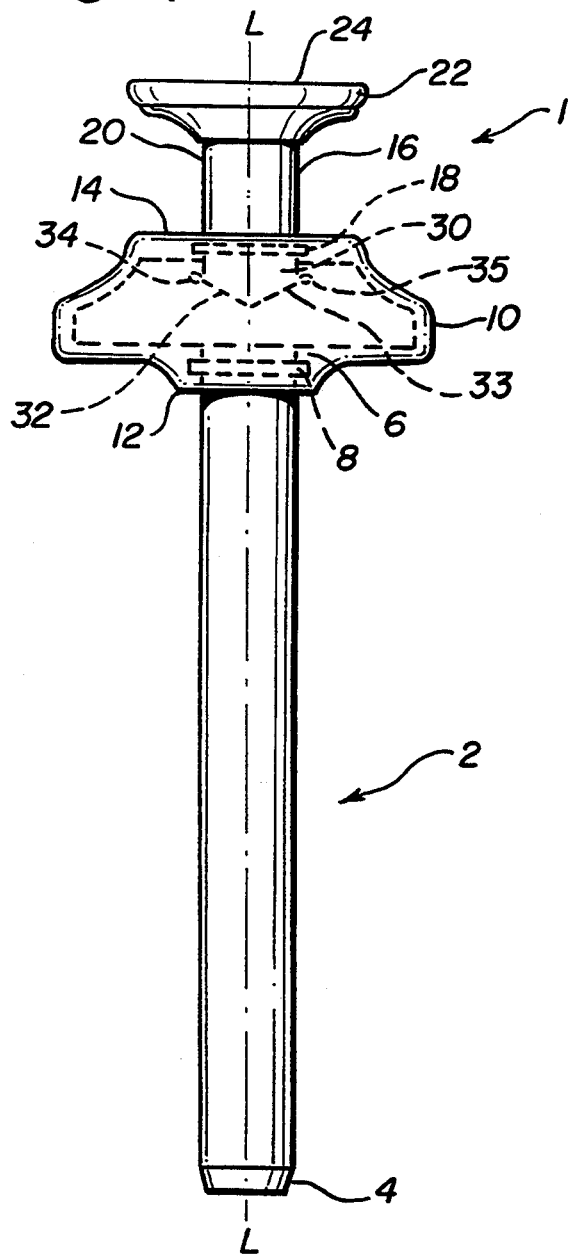
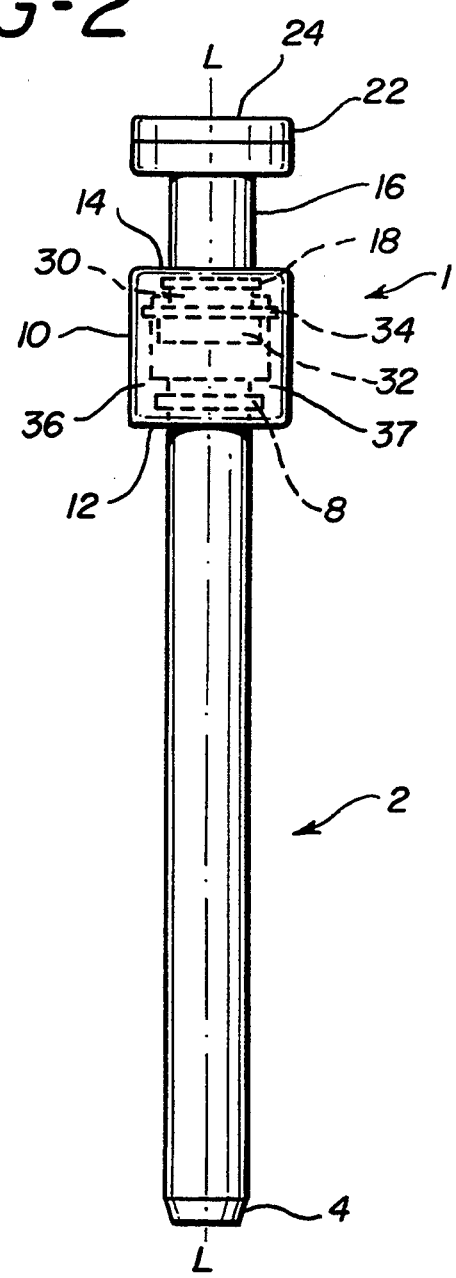

FLEXIBLE CANNULA

PRIORITY DATE

This application claims priority from DE P 42 34 990.7 filed Oct. 16, 1992.

BACKGROUND OF THE INVENTION

Conventional rigid cannulae which are used in endoscopic operations consist of a tube, whose distal zone is introducible into the inside of the body through a trocar puncture point, and a top piece which is attached to the proximal end of the tube. At its proximal end face the top piece has an opening, essentially aligned with the cross-section surface of the tube, to which is allocated a seal engaging at the shaft of introduced operation instruments. Located in the inside of the top piece is a closure device for the separate closing of the opening. Additional equipment, for example: (1) a trocar with which the puncture point is produced in the body wall and which is withdrawn from the cannula following the insertion of the cannula into the body wall; or (2) a reduction cap with seal for the use of instruments whose external diameter is much smaller than the internal diameter of the cannula, can be secured on the proximal end face of the top piece with the help of coupling elements.

In the case of operations in the abdominal area in particular, a gas is introduced into the inside of the body in order that the organs detach from the body wall. A gas connection with a valve can be provided at the top piece of the cannula for this purpose. If no surgical instrument is introduced into the cannula, the closure device is closed, so that the compressed gas cannot escape. Upon insertion of an instrument, the aforementioned seal engages at its shaft so that an escape of gas is similarly prevented.

A disadvantage with the previously known cannula is that it does not permit the introduction of curved instruments. At best, very thin and only slightly curved instruments can be inserted into a rigid large-diameter cannula. Attempts are thus being made to develop instruments having joints or hinges which are straight when guided through the cannula and whose distal zone is then bent in the inside of the body. Instruments with hinges are of a very costly design, however; for example, they require internal actuating systems in order to allow movement in the distal zone. Such instruments consequently have a larger shaft diameter, an can thus be introduced only through large cannulae which are generally less advantageous for the patient than small-diameter cannulae. Their elaborate design also makes them more expensive to produce.

Cannulae with a flexible tube are known for operations in the thorax region. Upon entry of air into the inside of the thorax, the wings of the lung change their shape and the organs are readily accessible for the operation; hence no compressed gas is required for such operations. There is thus no need for a separate closure device in the top piece of the cannula, so that the top piece can be designed without difficulties. A rigid design of the top piece is also possible in this case, which, together with a flat design, does not impede the introduction of curved operation instruments. By contrast, the top piece of the initially described conventional rigid cannula has a substantial structural height, so that simply replacing the conventional rigid tube by a flexible tube would not result in a flexible cannula which permits the insertion of curved instruments.

SUMMARY OF THE INVENTION

The object of the invention is to modify the previously described conventional rigid cannula further in such a way that the use of curved instruments for endoscopic applications is made possible.

This object is achieved by a flexible cannula with a tube made from a flexible material, and the top piece is designed flat when seen in the direction of the longitudinal axis of the tube, this being achievable through a suitable structure for the closure device (valve) and coupling elements. As a result of the flat design of the top piece, a guiding of curved shaft instruments through the top piece is not impeded, and the flexible tube adapts to the shape of the instrument. The principal features of this variation are the low structural height and favourable costs.

The tube is made from a flexible material, and the top piece is designed so that it is itself flexible. To this end, the top piece is divided into three parts: secured at the proximal end of the tube is a housing, flat when seen in the direction of the longitudinal axis of the cannula, which contains the valve device. Starting from the proximal end wall of the housing, a flexible intermediate tube extends along the longitudinal axis of the cannula. Finally, attached to the proximal end of the flexible intermediate tube is a coupling part which comprises the opening and the coupling elements. The seal is preferably designed as a flexible plastic disc surrounding the opening and is thus also arranged in the coupling part. The accommodation of the functional elements, namely the closure device and the coupling elements, in separate units allows these to be designed flat, which does not impede the insertion of a curved surgical instrument. The flexible intermediate tube running between the housing and the coupling part allows a relative movement of the housing and of the coupling part with respect to each other, as is necessary for insertion of a curved instrument. The flexible cannula according to the invention is reliable in its mode of operation and also simple in design, i.e. inexpensive to produce. It can also be of advantage when using straight instruments, as the instrument head can be moved over a greater radius in the endoscopic operative field because of the flexibility of the cannula.

In an advantageous version, the closure (valve) device is designed as a flap closure, preferably as a double flap which elastically abuts against the distal edge of a closure sleeve essentially aligned with the opening. The wings of the double flap come together at their free ends on the longitudinal axis of the cannula and are hinged at the opposed ends. The wings are able to be forced away in a distal direction upon introduction of a surgical instrument. This version leads to a low structural height, and is more desirable than a single flap which must have a greater length in order to achieve a closure effect. The closure device can also be designed as a flat slide valve.

There is sufficient space at the side walls of the top piece or housing for a gas connection without impairing flexibility. The flexible cannula according to the invention thus also makes possible the supply of gas into the inside of the body, and it is not necessary to switch to other cannulae during the operation for this purpose.

DESCRIPTION OF THE DRAWINGS

The invention is described in more detail with reference to a non-limitative embodiment.

The drawings show:

FIG. 1 a side view, in partial sectional view, of a flexible cannula according to the invention, FIG. 2 a side view, in partial sectional view, of the flexible cannula from FIG. 1, rotated by 90 degrees compared with the representation in FIG. 1, FIG. 3 a top view of the coupling part of the flexible cannula represented in FIGS. 1 and 2, and FIG. 4 a side view, in partial cross section, from the same direction of view as in FIG. 1, in which a trocar insert is introduced into the flexible cannula represented in FIGS. 1 to 3.

DETAILED DESCRIPTION OF THE INVENTION

Figure 4:
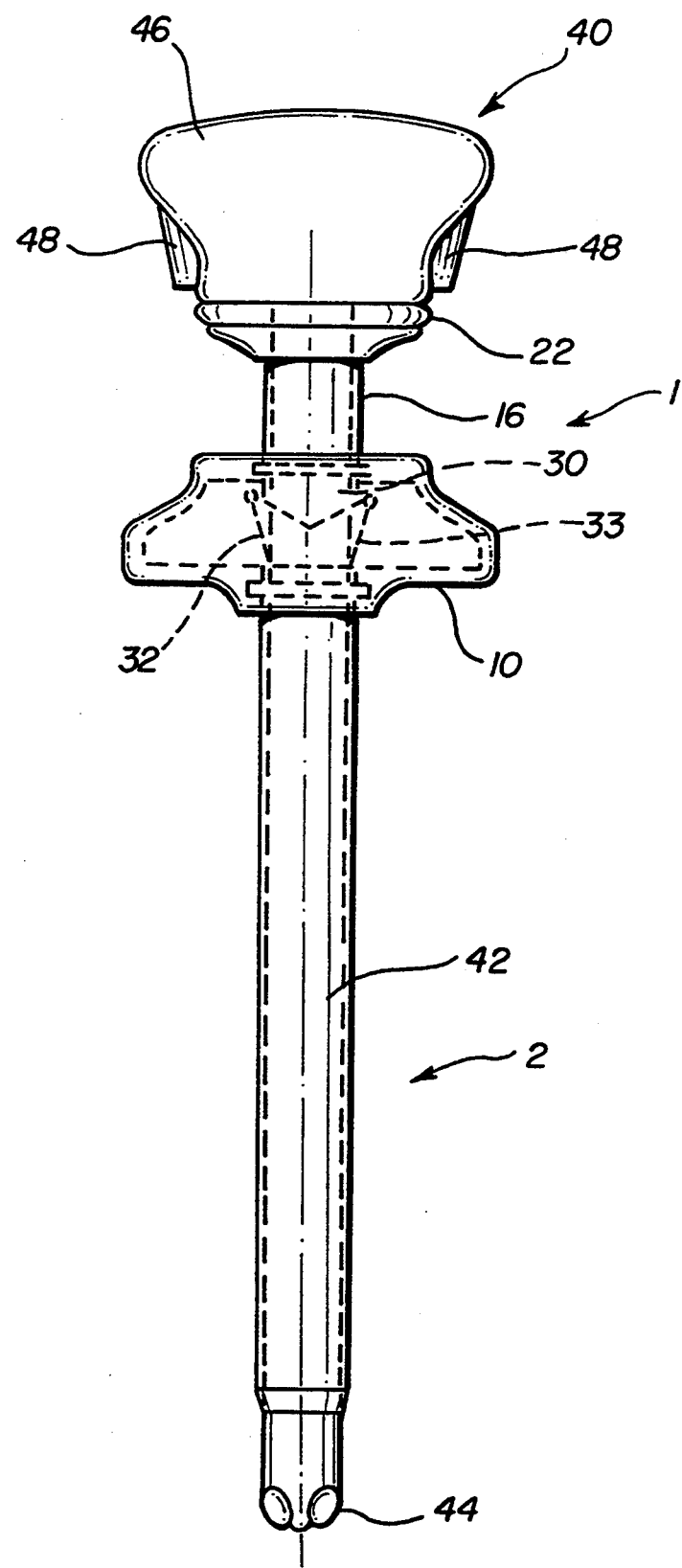

The version of a flexible cannula according to the invention shown in FIG. 1 consists of a top piece 1 and a tube 2. The tube 2 has essentially the shape of a hollow cylinder and can be bevelled at its distal end 4. Attached in the vicinity of its proximal end 6, on the outside of the tube 2 is an annular protrusion 8 with the help of which the tube 2 is secured at the top piece 1. The tube 2 is made from a flexible material.

A housing 10 with a distal end wall 12 and a proximal end wall 14 is joined to the proximal end 6 of the tube 2. The distal end wall 12 is provided with an opening 30 which is concentric to the longitudinal axis L—L of the cannula and whose diameter is the same as the diameter of the tube 2. An annular recess for housing the protrusion 8 runs around the opening. The housing 10 preferably consists of two housing halves which are connected to each other in gas-tight manner, for example glued, so that the assembling of the tube 2 is simple, despite the protrusion 8.

A flexible intermediate tube 16 with an annular protrusion 18 is mounted in the proximal end wall 14, similar to the attachment of the tube 2 to the distal end wall 12. The intermediate tube 16 is made from a flexible material and runs concentrically relative to the longitudinal axis L—L. Its internal diameter can be the same as that of the tube 2, but can also be greater.

The intermediate tube 16 carries a coupling part 22 at its proximal end 20. As can be seen in FIG. 3, the proximal end face 24 of the coupling part 22 is provided with an opening 26. The opening 26 in the proximal end face 24 is essentially aligned with the cross-section surface of the tube 2; the diameter of the opening 26 can be somewhat greater than the internal diameter of the tube 2. In the embodiment, the opening 26 is surrounded by an annular seal 27 which is made from a flexible plastic material. The internal diameter of the seal 27 is preferably smaller than the internal diameter of the tube 2. The result of this is that the seal 27 lies securely against the shaft of an operation instrument introduced through the opening 26, even if the diameter of the shaft should be somewhat smaller than the internal diameter of the tube 2. On the other hand, the somewhat greater diameter of the opening 26, acting together with the flexible seal 27, permits a certain mobility for the inserted endoscopic operation instrument. The seal could also be designed differently, e.g. as an O-ring arranged further displaced in the distal direction.

Located at the proximal end face 24 are coupling elements 28 for securing additional equipment (such as e.g. a trocar or a reduction cap) which can be fitted onto the proximal end face 24. In the embodiment, the coupling elements are designed as two recesses 28, provided with projections, in the wall of the coupling part 22. The projections are engaged by corresponding projections at securing clips which are attached to the additional equipment to be fitted, so that a secure mechanical connection results. The connection can be released in the usual way by moving the distal end zones of the securing clips with the corresponding projections onto the axis L—L.

A closure device is arranged in the inside of the housing 10. A part of this closure device is a closure sleeve 30. In the embodiment, the closure sleeve 30 is designed in one piece with the flexible intermediate tube 16 and is thus held via the annular protrusion 18. The closure sleeve 30 has the same internal diameter as the flexible intermediate tube 16 and is cut at an angle on both sides, as shown in FIG. 1. The distal edge of the closure sleeve 30 forms a sealing surface against which two planar plates can lie, the angle between the plates being smaller than 180 degrees, see FIG. 1. Here the wings 32 and 33 of a double flap serve as sealing plates. Arranged at a distance from the longitudinal axis L—L (which is greater than the external radius of the closure sleeve 30) are a bearing element 34 connected to wing 32 and a bearing element 35 connected to wing 33.

The ends of the bearing elements 34, 35 are placed in corresponding recesses in side walls 36 and 37 of housing 10, see FIG. 2. As FIG. 2 also shows, the length of the wings 32 (hatched in FIG. 2) and 33 is great enough to cover the closure sleeve 30 completely, while on the other hand there is enough play in the housing 10 to allow a free swivel movement of the wings 32 and 33. The wings 32 and 33 are pressed against the distal edge of the closure sleeve 30 by springs which are not shown in the Figures. In order to achieve an adequate sealing effect, the distal edge of the closure sleeve 30 can be provided with a seal lining; alternatively, wings 32 and 33 can also be appropriately equipped. At their free ends, wings 32 and 33 meet on the longitudinal axis L—L, where they likewise form a sealing surface.

Upon introduction of an operation instrument into the flexible cannula, its distal end pushes the two wings 32 and 33 against the elastic force in the distal direction. When the instrument is withdrawn, the wings 32 and 33 automatically close under the action of the springs and thus prevent compressed gas from escaping from the inside of the body.

In order that the closure device can also be actuated manually, both bearing elements 34 and 35 can, for example, be guided through the side wall 36 or 37 on one side in gas-tight manner. If a lever is attached in each case to the outward-lying ends, wings 32 and 33 can easily be folded away in distal direction. Alternatively, only one of the bearing elements 34 or 35 could be passed through one of the side walls 36 or 37 if the two wings 32 and 33 are so coupled in the inside of the housing 10 that the swivelling of the wing connected to the passed-through bearing element simultaneously effects the swivelling of the other wing. The double flap can also be so designed that the wings 32 and 33 come together at an angle of 180 degrees, i.e., that the distal edge of the closure sleeve 30 lies in one plane. The advantage of designing the closure device as a double flap is the small axial structural height.

In an alternative version, the closure device is a flat slide valve. Flat slide valves are known, for example from vacuum technology. In a flat slide valve, opening or closure is effected by moving a flat closure part in a direction which runs essentially perpendicular to the axis of the opening to be closed, so that a small structural height is possible in the direction of this axis. As a flat slide valve cannot be opened directly from the distal end of an operation instrument which is moved essentially along the longitudinal axis, it must be actuated separately. This can take place manually, for example.

A usual gas connection with a valve or a manual actuation system for supplying gas into the inside of the body can be provided at the side wall 36 or side wall 37 of the housing 10.

The tube 2 and the intermediate tube 16 are made from a flexible material suitable for medical purposes, for example silicone or polyurethane.

The individual parts of the flexible cannula according to the invention are so fitted together that, when the closure device is closed, a space which is sealed off in a gas-tight manner is formed underneath the closure device, which space communicates with its surroundings only via the opening at the distal end 4 of the tube 2. When the closure device is opened and an operation instrument inserted, the seal 27 which lies against the shaft of the introduced endoscopic operation instrument.

FIG. 4 shows the inventive flexible cannula according to the described embodiment together with an introduced trocar 40. The trocar 40 has a shaft 42 whose external diameter corresponds to the internal diameter of the tube 2 or is somewhat smaller. At its distal end, the shaft 42 carries a trocar point 44 with the help of which a puncture point is produced in the body wall. Attached to the proximal end of the shaft 42 is a handling part 46 which serves to advance the trocar point 44. Attached to the handling part 46 and serving as coupling elements are two securing clips which can be pressed inwards with the help of two push buttons 48 in order to release the connection, as described earlier. It can be seen from FIG. 4 how the shaft 42 of the trocar 40, similarly to the shaft of another introduced endoscopic operation instrument, opens the wings 32 and 33 of the closure device. Where appropriate, additional equipment other than the trocar 40 can also be connected to the flexible cannula according to the invention via the coupling part 22.

In an alternative version of a flexible cannula according to the invention, the tube is made from a flexible material and the top piece is designed flat when seen in the direction of the longitudinal axis of the cannula. In this case, the top piece is not divided into several components as in the previous embodiment, but both the closure device and the opening at the proximal end face with the associated seal and the coupling elements are integrated in a single housing which is attached to the proximal end of the tube. In this embodiment, there is no flexible intermediate tube provided. In order to make possible the flat mode of construction of the housing, the closure device can be designed for example as a space-saving double flap of the type described above or as a flat slide valve. Because of the small extension of the top piece in the direction of the longitudinal axis of the cannula, the introduction of a curved operation instrument is not impeded, although the top piece itself is rigid.

We claim:

1. Flexible cannula with a tube whose distal zone is introducible into the inside of the body through a trocar puncture point, and with a top piece attached to its proximal end, the top piece having a proximal end face with an opening and a seal capable of engaging surgical instruments, and which is separately closeable by a closure device arranged in the inside of the top piece, said cannula characterized in that the tube is made from a flexible material and that the top piece is divided into a housing which has a flat proximal end and contains the closure device; and a flexible intermediate tube which, starting from the proximal end of the housing, extends along the longitudinal axis of the cannula.

2. Flexible cannula according to claim 1, characterized in the said seal is a flexible plastic disc surrounding the opening.

3. Flexible cannula according to claim 1, characterized in that the closure device is a flap closure.

4. Flexible cannula according to claim 1, characterized in that the tube is made from a flexible material and that the top piece is designed flat when seen in the direction of the longitudinal axis of the cannula.

5. Flexible cannula according to claim 1, characterized in that the wings meet at an angle of less than 180 degrees.

6. Flexible cannula according to claim 1, characterized in that said tube and said flexible intermediate tube are made from silicone.

7. Flexible cannula according to claim 1, characterized in that the tube and said flexible intermediate tube are made from polyurethane.

8. A trocar cannula comprising:
   a flexible distal tube, said distal tube insertable through the body through a trocar puncture point;
   a top piece attached to said distal tube; said top piece having a proximal opening and a seal capable of engaging surgical instruments; and
   said top piece containing a flexible intermediate tube contained within a housing, said flexible intermediate tube extending along the longitudinal axis in the direction of said distal tube.

* * * * *